United States Patent
Kassem (10) Patent No.: US 10,265,509 B2
(45) Date of Patent: Apr. 23, 2019

(54) WIRELESS SHUNTS WITH STORAGE

(71) Applicant: DePuy Synthes Products, LLC, Raynham, MA (US)

(72) Inventor: Salim Kassem, North Attleboro, MA (US)

(73) Assignee: INTEGRA LIFESCIENCES SWITZERLAND SARL, Le Locle (CH)

( * ) Notice: Subject to any disclaimer, the term of this patent is extended or adjusted under 35 U.S.C. 154(b) by 1434 days.

(21) Appl. No.: 13/848,295

(22) Filed: Mar. 21, 2013

(65) Prior Publication Data

US 2013/0226068 A1 Aug. 29, 2013

Related U.S. Application Data

(62) Division of application No. 11/931,187, filed on Oct. 31, 2007, now Pat. No. 8,480,612.

(51) Int. Cl.
*A61M 5/00* (2006.01)
*A61M 27/00* (2006.01)
(Continued)

(52) U.S. Cl.
CPC .......... *A61M 27/002* (2013.01); *A61B 5/0031* (2013.01); *A61B 5/031* (2013.01);
(Continued)

(58) Field of Classification Search
CPC ........ A61M 2205/3523; A61M 27/006; A61B 5/031
(Continued)

(56) References Cited

U.S. PATENT DOCUMENTS 2,396,351 A 3/1946 Thompson
3,886,948 A 6/1975 Hakim
(Continued)

FOREIGN PATENT DOCUMENTS

AU 729467 2/2001
CN 2555770 Y 6/2003
(Continued)

OTHER PUBLICATIONS

[No Author Listed] Surface Micromachined Pressure Sensor Technologies, product data sheet of Institut Mikroelektronische Schaultungen und Systeme, pp. 1-2, Sep. 2002.
(Continued)

*Primary Examiner* — Ariana Zimbouski
(74) *Attorney, Agent, or Firm* — Mintz Levin Cohn Ferris Glovsky and Popeo, P.C.

(57) ABSTRACT

Devices and methods useful for storing and retrieving information related to a medical device such as an implantable valve or an implantable sensor are disclosed. An implantable valve can include a valve housing adapted to receive fluid flow therethrough between a valve inlet and a valve outlet. A valve assembly can be disposed within the valve housing and adapted to control a rate of fluid flowing through the valve housing. The implantable valve can also include a radio frequency identification (RFID) tag associated with the valve housing, adapted to store data, and including an antenna for communicating stored data to an external reading device. The RFID tag can store data related to, for example, a patient, a pressure setting of the valve assembly, and/or pressure sensor disposed within the valve. The RFID tag can also store an identifier that identifies the implantable valve, a pressure sensor disposed in the valve housing, a patient associated with the implantable valve, and/or patient clinical history.

17 Claims, 6 Drawing Sheets

(51) Int. Cl.
  *A61B 5/00* (2006.01)
  *A61B 5/03* (2006.01)
  *A61M 39/22* (2006.01)
(52) U.S. Cl.
  CPC .......... *A61M 27/006* (2013.01); *A61M 39/22* (2013.01); *A61M 2205/04* (2013.01); *A61M 2205/32* (2013.01); *A61M 2205/3331* (2013.01); *A61M 2205/3344* (2013.01); *A61M 2205/3523* (2013.01); *A61M 2205/52* (2013.01)
(58) Field of Classification Search
  USPC ......... 604/7–10, 228; 600/488; 251/65, 177, 251/228; 137/530, 531
  See application file for complete search history.

(56) References Cited

U.S. PATENT DOCUMENTS

| | | |
|---|---|---|
| 3,960,142 A | 6/1976 | Elliott et al. |
| 3,976,278 A | 8/1976 | Dye et al. |
| 4,077,882 A | 3/1978 | Gangemi |
| 4,114,603 A | 9/1978 | Wilkinson |
| 4,127,110 A | 11/1978 | Bullara |
| 4,135,509 A | 1/1979 | Shannon |
| 4,237,900 A | 12/1980 | Schulman et al. |
| 4,332,255 A | 6/1982 | Hakim et al. |
| 4,385,636 A | 5/1983 | Cosman |
| 4,387,715 A | 6/1983 | Hakim et al. |
| 4,421,124 A | 12/1983 | Marshall |
| 4,494,950 A | 1/1985 | Fischell |
| 4,540,400 A | 9/1985 | Hooven |
| 4,551,128 A | 11/1985 | Hakim et al. |
| 4,556,086 A | 12/1985 | Raines |
| 4,576,181 A | 3/1986 | Wallace et al. |
| 4,593,703 A | 6/1986 | Cosman |
| 4,595,390 A | 6/1986 | Hakim et al. |
| 4,611,578 A | 9/1986 | Heimes |
| 4,615,691 A | 10/1986 | Hakim et al. |
| 4,625,730 A | 12/1986 | Fountain et al. |
| 4,660,568 A | 4/1987 | Cosman |
| 4,676,772 A | 6/1987 | Hooven |
| 4,711,249 A | 12/1987 | Brooks |
| 4,718,425 A | 1/1988 | Tanaka et al. |
| 4,723,556 A | 2/1988 | Sussman |
| 4,727,887 A | 3/1988 | Haber |
| 4,772,257 A | 9/1988 | Hakim et al. |
| 4,785,822 A | 11/1988 | Wallace |
| 4,787,886 A | 11/1988 | Cosman |
| 4,820,265 A | 4/1989 | DeSatnick et al. |
| 4,841,977 A | 6/1989 | Griffith et al. |
| 4,850,358 A | 7/1989 | Millar |
| 4,885,002 A | 12/1989 | Watanabe et al. |
| 4,893,630 A | 1/1990 | Bray, Jr. |
| 5,004,472 A | 4/1991 | Wallace |
| 5,009,662 A | 4/1991 | Wallace et al. |
| 5,021,046 A | 6/1991 | Wallace |
| 5,163,904 A | 11/1992 | Lampropoulos et al. |
| 5,201,753 A | 4/1993 | Lampropoulos et al. |
| 5,252,962 A | 10/1993 | Urbas et al. |
| 5,265,606 A | 11/1993 | Kujawski |
| 5,280,789 A | 1/1994 | Potts |
| 5,321,989 A | 6/1994 | Zimmer et al. |
| 5,337,612 A | 8/1994 | Evans |
| 5,385,514 A | 1/1995 | Dawe |
| 5,396,899 A | 3/1995 | Strittmatter |
| 5,417,235 A | 5/1995 | Wise et al. |
| 5,425,713 A | 6/1995 | Taylor et al. |
| 5,431,057 A | 7/1995 | Zimmer et al. |
| 5,431,629 A | 7/1995 | Lampropoulos et al. |
| 5,437,627 A | 8/1995 | Lecuyer |
| 5,449,345 A | 9/1995 | Taylor et al. |
| 5,490,514 A | 2/1996 | Rosenberg |
| 5,591,171 A | 1/1997 | Brown |
| 5,622,869 A | 4/1997 | Lewis et al. |
| 5,630,836 A | 5/1997 | Prem et al. |
| 5,643,194 A | 7/1997 | Negre |
| 5,651,767 A | 7/1997 | Schulman et al. |
| 5,704,352 A | 1/1998 | Tremblay et al. |
| 5,711,302 A | 1/1998 | Lampropoulos et al. |
| 5,716,342 A | 2/1998 | Dumbraveanu et al. |
| 5,721,382 A | 2/1998 | Kriesel et al. |
| 5,797,403 A | 8/1998 | DiLorenzo |
| 5,803,917 A | 9/1998 | Butterfield et al. |
| 5,836,886 A | 11/1998 | Itoigawa et al. |
| 5,873,840 A | 2/1999 | Neff |
| 5,928,182 A | 7/1999 | Kraus et al. |
| 5,935,083 A | 8/1999 | Williams |
| 5,970,801 A | 10/1999 | Ciobanu et al. |
| 5,993,395 A | 11/1999 | Shulze |
| 5,993,398 A | 11/1999 | Alperin |
| 6,010,482 A | 1/2000 | Kriesel et al. |
| 6,025,725 A | 2/2000 | Gershenfeld et al. |
| 6,071,267 A | 6/2000 | Zamierowski |
| 6,083,174 A | 7/2000 | Brehmeier-Flick et al. |
| 6,111,520 A | 8/2000 | Allen et al. |
| 6,113,553 A | 9/2000 | Chubbuck |
| 6,120,457 A | 9/2000 | Coombes et al. |
| 6,158,965 A | 12/2000 | Butterfield et al. |
| 6,171,252 B1 | 1/2001 | Roberts |
| 6,208,254 B1 | 3/2001 | McQueen et al. |
| 6,248,080 B1 | 6/2001 | Miesel et al. |
| 6,264,612 B1 | 7/2001 | McConnell et al. |
| 6,278,379 B1 | 8/2001 | Allen et al. |
| 6,316,522 B1 | 11/2001 | Loomis et al. |
| 6,371,976 B1 | 4/2002 | Vrzalik et al. |
| 6,416,291 B1 | 7/2002 | Butterfield et al. |
| 6,439,538 B1 | 8/2002 | Ito |
| 6,447,449 B1 | 9/2002 | Fleischman et al. |
| 6,470,213 B1 | 10/2002 | Alley |
| 6,481,292 B1 | 11/2002 | Reich |
| 6,503,208 B1 | 1/2003 | Skovlund et al. |
| 6,533,733 B1 * | 3/2003 | Ericson et al. ............... 600/561 |
| 6,537,232 B1 | 3/2003 | Kucharczyk et al. |
| 6,589,189 B2 | 7/2003 | Meyerson et al. |
| 6,626,902 B1 | 9/2003 | Kucharczyk et al. |
| 6,636,769 B2 | 10/2003 | Govari et al. |
| 6,682,490 B2 | 1/2004 | Roy et al. |
| 6,724,310 B1 | 4/2004 | Gershenfeld et al. |
| 6,731,976 B2 | 5/2004 | Penn et al. |
| 6,770,030 B1 | 8/2004 | Schaupp et al. |
| 6,796,942 B1 | 9/2004 | Kreiner et al. |
| 6,855,115 B2 | 2/2005 | Fonseca et al. |
| 6,891,474 B1 | 5/2005 | Fletcher |
| 6,974,422 B1 | 12/2005 | Millar |
| 7,147,604 B1 | 12/2006 | Allen et al. |
| 7,435,229 B2 | 10/2008 | Wolf |
| 7,485,105 B2 | 2/2009 | Wolf |
| 7,842,004 B2 | 11/2010 | Kassem |
| 2002/0035331 A1 | 3/2002 | Brockway et al. |
| 2002/0038072 A1 | 3/2002 | Muller et al. |
| 2002/0052563 A1 | 5/2002 | Penn et al. |
| 2002/0077553 A1 | 6/2002 | Govari et al. |
| 2002/0087059 A1 | 7/2002 | O'keefe |
| 2002/0099428 A1 | 7/2002 | Kaufman |
| 2002/0151770 A1 | 10/2002 | Noll et al. |
| 2003/0023134 A1 | 1/2003 | Tracey |
| 2003/0032915 A1 | 2/2003 | Saul |
| 2003/0135110 A1 | 7/2003 | Leussler |
| 2003/0216666 A1 | 11/2003 | Ericson et al. |
| 2004/0073137 A1 | 4/2004 | Lloyd et al. |
| 2004/0134991 A1 | 7/2004 | Fletcher et al. |
| 2004/0147871 A1 | 7/2004 | Burnett |
| 2004/0193021 A1 | 9/2004 | Zdeblick et al. |
| 2004/0260229 A1 | 12/2004 | Meir |
| 2005/0027330 A1 | 2/2005 | Govari |
| 2005/0043669 A1 | 2/2005 | Rosenberg |
| 2005/0043670 A1 | 2/2005 | Rosenberg |
| 2005/0165317 A1 | 7/2005 | Turner et al. |
| 2005/0187487 A1 | 8/2005 | Azizkhan et al. |
| 2005/0187488 A1 | 8/2005 | Wolf |
| 2005/0187509 A1 | 8/2005 | Wolf |
| 2005/0197585 A1 | 9/2005 | Brockway et al. |

(56) References Cited

U.S. PATENT DOCUMENTS

| | | | |
|---|---|---|---|
| 2005/0204811 | A1 | 9/2005 | Neff |
| 2005/0247319 | A1* | 11/2005 | Berger ............... 128/898 |
| 2005/0277839 | A1 | 12/2005 | Alderman et al. |
| 2006/0009699 | A1 | 1/2006 | Roteliuk et al. |
| 2006/0020239 | A1 | 1/2006 | Geiger et al. |
| 2006/0036208 | A1 | 2/2006 | Burnett |
| 2006/0149161 | A1 | 7/2006 | Wilson et al. |
| 2006/0189888 | A1 | 8/2006 | Hassler et al. |
| 2006/0195043 | A1 | 8/2006 | Rutherford et al. |
| 2006/0211944 | A1 | 9/2006 | Mauge et al. |
| 2006/0211945 | A1 | 9/2006 | Mauge et al. |
| 2006/0211946 | A1* | 9/2006 | Mauge et al. ......... 600/488 |
| 2006/0212439 | A1* | 9/2006 | Field ............... G06F 11/1453 |
| 2006/0235310 | A1 | 10/2006 | O'Brien et al. |
| 2006/0283007 | A1 | 12/2006 | Cros et al. |
| 2007/0049845 | A1 | 3/2007 | Fleischman et al. |
| 2007/0118038 | A1 | 5/2007 | Bodecker et al. |
| 2007/0167867 | A1 | 7/2007 | Wolf |
| 2007/0208293 | A1 | 9/2007 | Mansour et al. |
| 2007/0210923 | A1* | 9/2007 | Butler et al. ......... 340/572.8 |
| 2007/0252691 | A1* | 11/2007 | Mirmobin et al. ..... 340/539.22 |
| 2007/0282210 | A1 | 12/2007 | Stern |
| 2008/0058652 | A1 | 3/2008 | Payne |
| 2008/0065646 | A1* | 3/2008 | Zhang ............... G06Q 10/00 |
| 2008/0139959 | A1 | 6/2008 | Miethke et al. |
| 2008/0208083 | A1 | 8/2008 | Lin et al. |
| 2008/0242944 | A1* | 10/2008 | Sharma ............... 600/300 |
| 2009/0107233 | A1 | 4/2009 | Kassem |
| 2009/0112103 | A1* | 4/2009 | Kassem ............... 600/488 |
| 2009/0112147 | A1 | 4/2009 | Kassem |
| 2009/0112308 | A1 | 4/2009 | Kassem |
| 2010/0168673 | A1 | 7/2010 | Stergiopulos et al. |
| 2011/0040233 | A1 | 2/2011 | Kassem |

FOREIGN PATENT DOCUMENTS

| | | | |
|---|---|---|---|
| DE | 4042335 | A1 | 8/1991 |
| DE | 4042336 | A1 | 8/1991 |
| EP | 0115548 | | 8/1984 |
| EP | 0619101 | A1 | 10/1994 |
| EP | 1312302 | | 5/2003 |
| EP | 1389477 | | 2/2004 |
| EP | 1491137 | | 12/2004 |
| EP | 1738792 | A1 | 1/2007 |
| JP | 02-003821 | A | 1/1990 |
| WO | 91/105575 | A1 | 5/1991 |
| WO | 99/53990 | A1 | 10/1999 |
| WO | 01/021066 | A1 | 3/2001 |
| WO | 2005/046467 | A1 | 5/2005 |
| WO | 2006/048664 | A2 | 5/2006 |
| WO | 2006117123 | | 11/2006 |
| WO | 2007/041843 | A1 | 4/2007 |
| WO | 2007081741 | A2 | 7/2007 |

OTHER PUBLICATIONS

[No Author Listed] User's Manual HD2114.0-HD2134.0, HD2164.0-HD2114B.0, HD2114, 2-HD2134.2, HD2164.2-HD2114B.2; Rev. 1.0, Delta OHM, Via g. Marconi, 5-35020 Caselle Di Selvazzano (PD)—Italy, pp. 2-6 (2004).

[No Author Listed] Telemetric Integrated Pressure Sensors, product data sheet of Institut Mikroelektronische Schaultungen und Systeme, p. 1, Sep. 2002.

Dobkin et al., "A Radio-Oriented Introduction to RFID-Protocols, Tags and Applications," High Frequency Electronics, 32-46 (2005).

Ekstedt, J., "CSFS Hydrodynamic Studies in Man, 1. Method of Constant Pressure CSF Infusion," J. Neurology, Neurosurgery & Psych.40:105-19 (1977).

European Search Report, Appl. No. 052580800.0, dated May 15, 2006.

European Search Report, EP Application No. 08253545.1-1526, dated Mar. 5, 2009.

European Search Report, EP Application No. 08253554, dated Feb. 19, 2009.

Ko WH et al: "Cerebrospinal Fluid Control System," Proceeding of the IEEE, IEEE. New York, US, vol. 76, No. 9, Sep. 1, 1988 (Sep. 1, 1988), pp. 1226-1235, XP000094517 ISSN: 0018-9219.

Kroin, JS, et al., "Long-term testing of an intracranial pressure monitoring device", J. Neurosurg, V. 93, pp. 852-858, 2000.

Sensor Transponder for Pressure and Temperature, data sheet of Institut Mikroelektronische Schaultungen und Systeme, pp. 1-2, Feb. 2000.

Shapiro, K. et al. "Characterization of Clinical CSF Dynamics and Neural Zxis Compliance Using the Pressure-Volume Index: 1. The Normal Pressure-Volume Index," Annals of Neurology, 7(6):508-14 (1980).

U.S. Office Action for U.S. Appl. No. 12/913,054 dated Nov. 26, 2012 (11 Pages).

U.S. Office Action for U.S. Appl. No. 11/931,041 (Publication No. US-2009-0107233-A1) dated Dec. 30, 2009, 19 pages.

U.S. Office Action for U.S. Appl. No. 11/931,127 dated May 10, 2012 (26 Pages).

U.S. Office Action for U.S. Appl. No. 11/931,151 dated Feb. 6, 2012.

U.S. Office Action for U.S. Appl. No. 11/931,151 dated Jul. 13, 2012 (23 pages).

U.S. Office Action for U.S. Appl. No. 11/931,151 dated Jul. 19, 2011, 23 pages.

U.S. Office Action for U.S. Appl. No. 11/931,151 dated Feb. 20, 2013, 25 pages.

U.S. Office Action for U.S. Appl. No. 11/931,187 dated Apr. 24, 2012 (10 Pages).

U.S. Office Action for U.S. Appl. No. 11/931,187 dated May 11, 2010, 8 pages.

U.S. Office Action for U.S. Appl. No. 11/931,187 dated May 9, 2011, 7 pages.

U.S. Office Action for U.S. Appl. No. 11/931,187 dated Oct. 31, 2011.

U.S. Office Action for U.S. Appl. No. 11/931,187 dated Oct. 6, 2010, 8 pages.

U.S. Office Action for U.S. Appl. No. 11/931,151 dated May 15, 2013, 21 pages.

\* cited by examiner

WIRELESS SHUNTS WITH STORAGE

CROSS REFERENCE TO RELATED APPLICATIONS

The present application is a divisional of U.S. patent application Ser. No. 11/931,187, filed on Oct. 31, 2007 and entitled "Wireless Shunts with Storage," which is hereby incorporated by reference in its entirety.

FIELD OF THE INVENTION

The present invention generally relates to devices and methods for non-invasively storing and accessing data related to medical devices, and more particularly to non-invasively storing and accessing data related to shunts.

BACKGROUND

It is often desirable to be able to provide data about medical devices and/or patients using them, particularly for implanted medical devices. By way of illustration, treatment of hydrocephalus can involve implanting medical devices in a body, and a caregiver may need access data about the implanted device, the patient in which the device is implanted, or data generated by the device. Hydrocephalus is a neurological condition that is caused by the abnormal accumulation of CSF within the ventricles, or cavities, of the brain. CSF is a clear, colorless fluid that is primarily produced by the choroid plexus and surrounds the brain and spinal cord. CSF constantly circulates through the ventricular system of the brain and is ultimately absorbed into the bloodstream. CSF aids in the protection of the brain and spinal cord. Because CSF keeps the brain and spinal cord buoyant, it acts as a protective cushion or "shock absorber" to prevent injuries to the central nervous system.

Hydrocephalus, which affects children and adults, arises when the normal drainage of CSF in the brain is blocked in some way. Such blockage can be caused by a number of factors, including, for example, genetic predisposition, intra-ventricular or intra-cranial hemorrhage, infections such as meningitis, head trauma, or the like. Blockage of the flow of CSF consequently creates an imbalance between the amount of CSF produced by the choroid plexus and the rate at which CSF is absorbed into the bloodstream, thereby increasing pressure on the brain, which causes the ventricles to enlarge.

Hydrocephalus is most often treated by surgically inserting a shunt system that diverts the flow of CSF from the ventricle to another area of the body where the CSF can be absorbed as part of the circulatory system. Shunt systems come in a variety of models, and typically share similar functional components. These components include a ventricular catheter which is introduced through a burr hole in the skull and implanted in the patient's ventricle, a drainage catheter that carries the CSF to its ultimate drainage site, and optionally a flow-control mechanism, e.g., shunt valve, that regulates the one-way flow of CSF from the ventricle to the drainage site to maintain normal pressure within the ventricles.

As noted above, one problem encountered with the use of shunt systems is the difficulty in accessing data related to a shunt system implanted in a patient. One current technique for accessing data involves recording data related to a shunt system in a patient's written medical file. While this technique is advantageous in that it centrally collects patient data, the written medical file is not always accessible, for example, if the patient has an emergency and is taken to a hospital without access to the written medical file. Furthermore, tracking historical data using this technique can be cumbersome.

Accordingly, there remains a need for storing and accessing data related to implanted medical devices, and particularly shunt systems.

SUMMARY

In one embodiment, an implantable valve is provided. The implantable valve can include a valve housing adapted to receive fluid flow therethrough between a valve inlet and a valve outlet. A valve assembly can be disposed within the valve housing and adapted to control a rate of fluid flowing through the valve housing. The implantable valve can also include a radio frequency identification (RFID) tag disposed within the valve housing and adapted to store data. The RFID tag can include an antenna for communicating stored data to an external reading device. The RFID tag can store data related to a patient. The RFID tag can also store an identifier that identifies the implantable valve, a pressure sensor disposed in the valve housing, and/or a patient associated with the implantable valve. Furthermore, the radio frequency identification tag can store a pressure setting of the valve assembly that controls the rate of fluid flowing through the valve housing.

A wide array of variations are possible. In some embodiments, the implantable valve can include a sensor disposed within the valve housing and adapted to measure a pressure of fluid flowing through the valve housing. In some embodiments, the radio frequency identification tag can store calibration data for calibrating pressure measured by the pressure sensor. In some embodiments, the radio frequency identification tag can be disposed a distance apart from the sensor. Alternatively, the radio frequency identification tag can be disposed proximate to any of the valve inlet of the valve housing and the valve outlet of the valve housing. In yet other embodiments, the radio frequency identification tag can be disposed proximate to a reservoir formed in the valve housing. In some embodiments, the RFID tag can be disposed by itself, without any pressure sensor.

In another embodiment, an implantable data storage system is provided which can have a pressure sensor adapted to measure a pressure of fluid in a housing. A radio frequency identification tag can be associated with the pressure sensor, and it can be adapted to store data related thereto. The RFID tag can also include an antenna for communicating stored data to an external reading device. In some embodiments, the pressure sensor can be disposed in a valve that is adapted to receive fluid flow therethrough between a valve inlet and a valve outlet. The pressure sensor can be disposed within the valve and the radio frequency identification tag can be associated with the valve. The radio frequency identification tag can be disposed in a body at a location remote from the pressure sensor or, in other embodiments, disposed within a housing of the pressure sensor. The radio frequency identification tag can store calibration data for calibrating pressure measured by the pressure sensor and/or data related to a patient's medical history. If a second sensor is also implanted (for example, a flow sensor or another pressure sensor), the radio frequency identification tag can be associated with a second sensor and be adapted to store data related to the second sensor as well. The pressure sensor and the radio frequency identification tag can be coated with a fluid-impermeable coating.

In other aspects, methods for storing and retrieving information related to an implantable valve are provided. In one embodiment, a method can include positioning a distal end of a ventricular catheter within a ventricle. The method can further include coupling a proximal end of the ventricular catheter to a valve inlet formed on an implantable valve and coupling a valve outlet formed on the valve to a drainage catheter such that fluid flows from the ventricle through the valve to the drainage catheter. The method can also include using an external reading device to obtain data telemetrically from a radio frequency identification tag disposed in the valve, for example, by positioning the external reading device in proximity to the radio frequency identification tag. The radio frequency identification tag can be adapted to store data related to the valve. In other embodiments, obtaining data can include obtaining data related to calibration data for the pressure sensor, patient data, patient clinical history, identification data for the valve, and/or identification data for a pressure sensor disposed within the valve.

In still other embodiments, the method can include adjusting a rate of fluid flow from the inlet valve to the outlet valve. The method can also include programming the radio frequency identification tag with an external reading device. In some embodiments, the radio frequency identification tag can store a pressure measurement obtained by a pressure sensor disposed within the valve. In other embodiments, the method can also include communicating with the pressure sensor and the radio frequency identification tag at a same frequency, or different frequencies, using an external reading device.

BRIEF DESCRIPTION OF THE DRAWINGS

The invention will be more fully understood from the following detailed description taken in conjunction with the accompanying drawings, in which.

DETAILED DESCRIPTION

Certain exemplary embodiments will now be described to provide an overall understanding of the principles of the structure, function, manufacture, and use of the devices and methods disclosed herein. One or more examples of these embodiments are illustrated in the accompanying drawings. Those skilled in the art will understand that the devices and methods specifically described herein and illustrated in the accompanying drawings are non-limiting exemplary embodiments and that the scope is defined solely by the claims. The features illustrated or described in connection with one exemplary embodiment may be combined with the features of other embodiments. Such modifications and variations are intended to be included within the scope of the present application.

Generally, methods and devices for storing and accessing data related to an implantable medical device, such as an implantable valve, are provided. The methods and devices are particularly useful in the context of valves for monitoring intra-ventricular pressure. In some embodiments, they can allow data related to a pressure sensor (or, for example, temperature or flow sensors) in an implantable valve to be stored on and retrievable from an implantable radio frequency identification (RFID) tag associated with a pressure sensor and/or an implantable valve, thereby providing convenient and reliable access to data related to the implantable valve. A person skilled in the art will appreciate that, while the methods and devices are described below in connection with an implantable valve for controlling cerebrospinal fluid and an associated pressure sensor, this description is by way of illustration only, and that the methods and devices can be used for a variety of medical procedures and in a variety of devices, including other kinds of sensors and/or sensors that are not disposed within valves.

Figure 1:
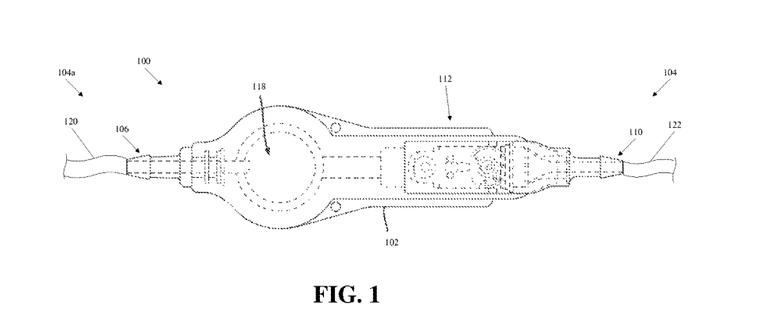
FIG. 1 is a top view of one exemplary embodiment of an implantable valve.
Figure 2:
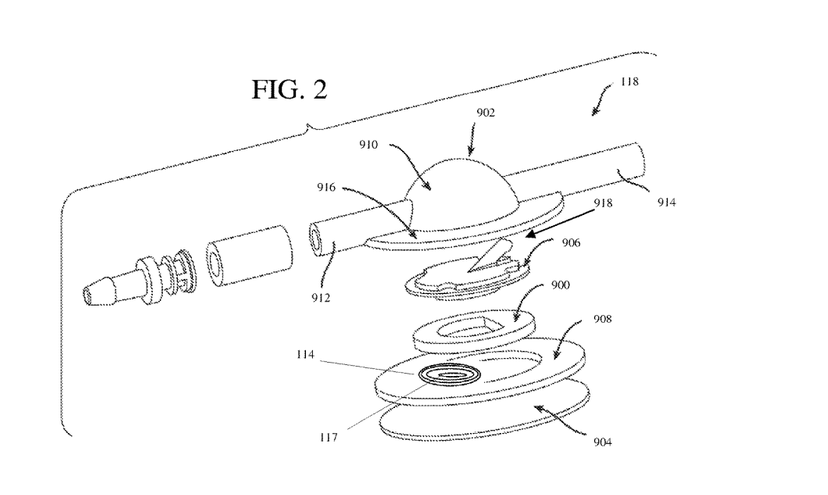
FIG. 2 is an exploded view of a portion of the implantable valve shown in FIG. 1.

FIGS. 1 and 2 illustrate one exemplary embodiment of an implantable valve 100 that includes a radio frequency identification (RFID) tag 114. The valve 100 can be used alone or in combination with a pressure sensor assembly 118 that has a pressure sensor 900 therein, and/or other pressure sensor assemblies disposed upstream or downstream of the valve 100. As shown the, RFID tag 114 can be disposed inside the valve 100, but in other embodiments, the RFID tag 114 can be disposed outside the valve or any distance apart from the valve and/or the sensor 900. In many embodiments, the RFID tag 114 can be offset from the pressure sensor to facilitate communication. As will be explained in more detail below, the RFID tag 114 can store and communicate data which, for example, can be related to, for example, the valve 100, the pressure sensor 900, and/or a patient.

While the implantable valve 100 can have virtually any configuration, and a variety of implantable valves known in the art can be used, as shown in FIG. 1 the implantable valve 100 has a valve housing 102 with proximal and distal ends 104a, 104b. The housing 102 can have virtually any configuration, shape, and size, preferably one making the housing 102 suitable for subcutaneous implantation. Fluid (e.g., CSF) can flow through the housing 102 from an inlet (fluid entry) port 106 at the proximal end 104a and out an outlet (fluid exit) port 110 at the distal end 104b. The location and size of the ports 106, 110 can vary, but in many embodiments they can be adapted to allow fluid to flow therethrough and into and out of the housing 102. The proximal and distal ends 104a, 104b of the valve 100 can each be open and adapted to couple to another medical device, such as a catheter. The valve housing 102 can contain a valve assembly 112 for controlling the flow of fluid from the inlet port 106 to the outlet port 110, and a pressure sensor assembly 118 for measuring a pressure of the fluid flowing through the valve 100, as will be described in more detail below with respect to FIG. 2. While the valve assembly 112 and the pressure sensor assembly 118 of the valve 100 are shown in-line with one another and with the inlet port 106 and outlet port 110, and the pressure sensor assembly 118 is positioned upstream of the valve 100, the valve 100 can have a variety of other configurations, and the valve assembly 112, the pressure sensor assembly 118, the inlet port 106, and the outlet port 110 can be positioned at various locations relative to one another. For example, the inlet port 106 can extend at a right angle with respect to the pressure sensor assembly 118 such that the inlet port 106 extends in a direction substantially transverse to a longitudinal axis of the valve 100. The valve assembly 112 can also have a variety of configurations. By way of non-limiting example, exemplary valves are described in U.S. Pat. Nos. 3,886,948, 4,332,255, 4,387,715, 4,551,128, 4,595,390, 4,615,691, 4,772,257, and 5,928,182, all of which are hereby incorporated by reference in their entireties.

As shown in FIG. 2, the pressure sensor assembly 118 can include the sensor 900, a sensor housing 902, a backing 904, and an RFID tag 114. The sensor housing 902 can have a variety of shapes and sizes, but in the illustrated exemplary embodiment the sensor housing 902 has a generally hemispherical or domed portion 910 that defines a reservoir therein. The sensor housing 902 can also include an inlet tube 912 that couples to the inlet port 106 of the valve 100, and an outlet tube 914 that couples to the outlet port 110 of the valve 100. When the sensor housing 902 is mated to the backing 904, the reservoir chamber defined by the housing 902 is sealed, thereby allowing fluid to flow from the inlet port 106 of the valve 100, through the sensor housing 902, through the valve 906, and out the outlet port 110 in the valve 100. The sensor housing 902 can also include a flange 916 formed around a base of the domed portion 910 to allow the device to be secured to tissue. For example, the flange 916 can include one or more suture holes formed therein for receiving suture to attach the flange 916 to tissue.

Figure 3:
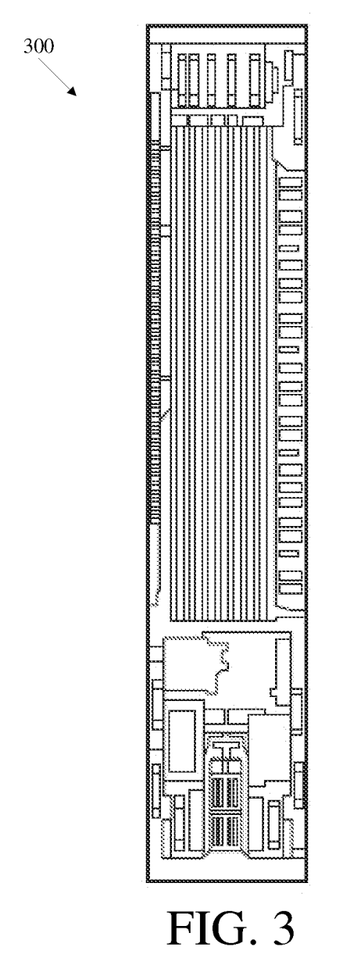
FIG. 3 is a top view of one exemplary embodiment of a pressure sensor.

The pressure sensor 900, such as the exemplary pressure sensor 300 shown in FIG. 3, can be formed on a microchip which can be coupled to an antenna 117 for communicating a sensed pressure to an external device. The antenna 117 can have a substantially circular shape, and the microchip sensor can be coupled to the antenna 117 which can, for example, be in the form of a gold microcoil. The sensor 900 and the RFID tag 114 can also each include a fluid-impermeable coating, as further described below, to protect the sensor 900 and the RFID tag 114 from fluid flowing through the sensor housing 902 or from other fluid. The size of sensor can vary, but in one exemplary embodiment the microchip sensor 900 has a size that is in the range of about 1 mm to 3 mm, and more preferably that is about 2.5 mm$^2$. Exemplary embodiments of a pressure sensor and antenna are described in more detail in U.S. Pat. No. 5,321,989, U.S. Pat. No. 5,431,057, EP Patent No. 1 312 302, and in co-pending, commonly assigned U.S. patent application Ser. No. 10/907,665, entitled "Pressure Sensing Valve" by Mauge et al., filed Apr. 11, 2005 (now published as U.S. Publication No. 2006-0211946 A1), all of which are hereby incorporated by reference.

In use, the sensor 900, which is disposed within the sensor housing 902, measures the pressure of fluid flowing through the sensor housing 902. In particular, the inlet port 106 of the valve 100 can be coupled to the ventricular catheter 120 for receiving fluid flow from one or more ventricles, and the outlet port 110 can be coupled to a drainage catheter 122. As fluid enters the sensor housing 902, the pressure of the fluid will apply a force to active sensor membranes formed on the sensor 900, thereby allowing the fluid pressure to be measured. The sensed pressure can be communicated, via the antenna, to an external reading device, as described further below. Performance of the sensor membranes can vary with factors such as temperature, its age, and its maintenance, and the membranes may need to be calibrated to correct for such variance. Calibration can vary from sensor to sensor. Calibration information, such as calibration coefficients and drift compensation values particular to the sensor 900, can be stored in the RFID tag 114 (as well as other kinds of information, which will be described in more detail below). Stored calibration information can be read by an external device, identified as associated with this particular sensor 900, and used to calibrate the sensor 900. An external reading device, e.g., a radio frequency ("RF") reader, can inductively couple to the RFID tag 114 and non-invasively communicate data for storage to the RFID tag 114 and/or non-invasively receive stored data from the RFID tag 114.

As shown, the sensor 900 and the RFID tag 114 can be disposed in the sensor housing 902, although the location of the RFID tag 114 can vary widely. For example, in other embodiments the RFID tag 114 can be remote from the sensor 900 and valve 100, for example, disposed outside the housing 902 or implanted in another area of the body. In many embodiments, the sensor 900 and the RFID tag 114 can be physically separate, without a physical link or connection (e.g., a mechanical, electrical, or communication link or connection) between them. Such an arrangement can allow for a flexible, independent design of, in this case, the sensor 900, valve 100, and RFID tag 114. For example, the valve 100 may be limited in size, and the RFID tag 114 can be located outside the valve 100 while the sensor 900 can be located within the valve 100. As another example, a sensor having a microchip (as described above in connection with FIG. 3) can dedicate the microchip to sensor functionality, and accordingly retain a relatively small size, while a separate RFID tag can provide storage related that sensor. In addition, in some embodiments the RFID tag can be "retrofitted" to previously implanted medical devices, for example, which were implanted without an RFID tag and do not have its storage and communication abilities. In some embodiments, even though the RFID tag and the pressure sensor, for example, are physically separate from one another (as in FIGS. 5-7, for example), their respective antennas can be located in proximity or adjacent to one another, so that both devices can be read with an external reading device in one location. The external reading device may communicate with each device using a different frequency, protocol, etc., as will be described in more detail below.

As shown in FIG. 2, the valve 100 (or other device in which the RFID tag 114 is embedded, or associated with) can have features to protect the RFID tag 114. For example, as shown in FIG. 2 the sensor assembly 118 of the valve 100 can include a washer 908, which can be provided to seat the sensor 900 and/or the RFID tag 114, such that the washer 908 and the sensor 900 and/or the RFID tag 114 are positioned against the backing 904. The washer 908 can also be configured such that the sensor 900 and/or the RFID tag 114 are sub-flush with the washer 908, for example, to protect the sensor 900 and the RFID tag 114 from potential damage when the domed portion 910 of the housing 902 is depressed. The sensor assembly 118 can also include a needle guard 906 for protecting the sensor 900 and the RFID tag 114. In particular, the needle guard 906 can protect the sensor 900 and the RFID tag 114 from coming into contact with the domed portion 910 of the housing 902 when the domed portion 910 is depressed, as the needle guard 906 can be positioned between the sensor 900 and the domed portion 910. The needle guard 906 can also be provided to protect the sensor 900 and the RFID tag 114 from a needle being inserted through the domed portion 910 of the sensor housing 902. While the shape of the needle guard 906 can vary, in an exemplary embodiment, as shown, the needle guard 906 has a substantially planar, circular shape and it is adapted to be disposed between the domed portion 910 of the housing 902 and the sensor 900. The needle guard 906 can, however, include an opening formed therein and positioned adjacent to the microchip sensor 900 to allow fluid flowing through the sensor housing 902 to come into contact with the sensor 900. In an exemplary embodiment, a flange or protective member 918 is disposed over the opening, without blocking the opening from fluid flow, to prevent a user from accidentally inserted a needle through the opening. Further information on these features can be found in U.S. Publication No. 2006-0211946 A1, referenced above.

Figure 4:
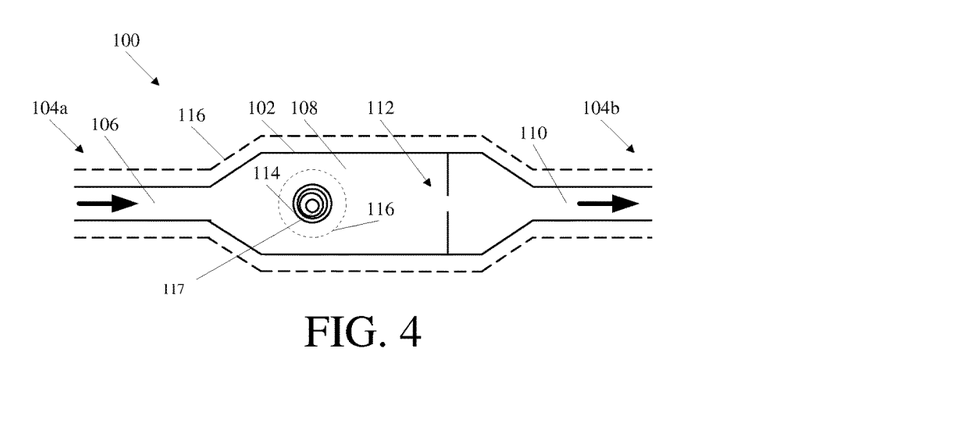
FIG. 4 is a schematic view of one exemplary embodiment of an implantable valve having an RFID tag disposed therein.

FIG. 4 is a schematic illustration of one embodiment of the implantable valve 100 of FIGS. 1 and 2 showing one possible location of the RFID tag 114 disposed within the housing 102. In this embodiment, the housing 102 has a substantially linear configuration with a reservoir 108 having a larger area than ports 106, 110, which can be advantageous for checking the shunt's patency, tapping the CSF, to administer therapy, or to house pressure or flow sensors. As indicated by directional arrows, fluid (e.g., CSF) can flow through the inlet port 106, through the reservoir 108, and out the outlet port 110. As shown, the RFID tag 114, for storing data and for communicating stored data, is disposed in the sensor housing 902 that defines the reservoir 108.

Figure 5:
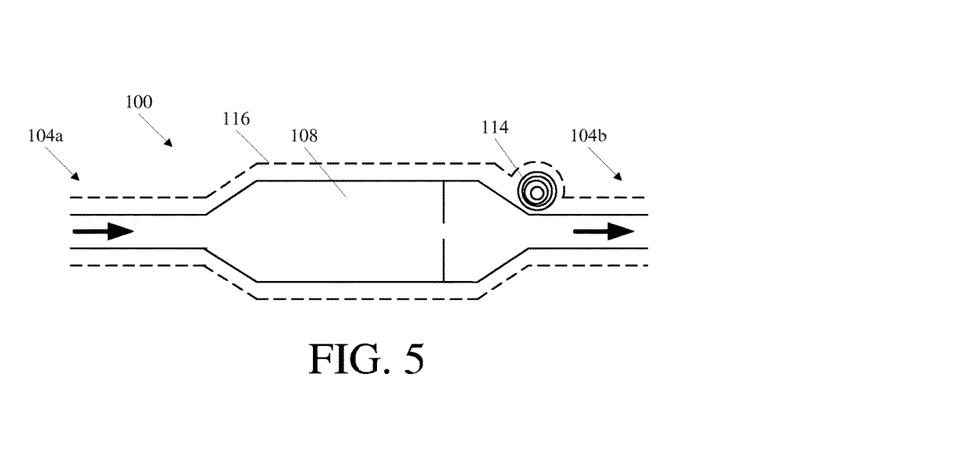
FIG. 5 is a schematic view of the valve shown in FIG. 4 with an RFID tag disposed in an alternate location.
Figure 6:
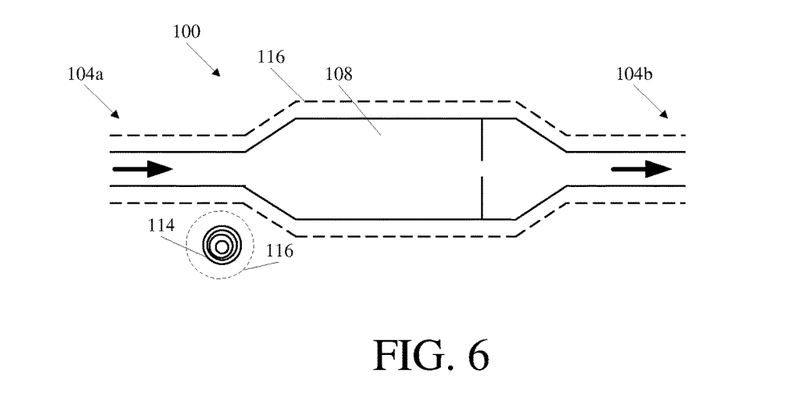
FIG. 6 is a schematic view of the valve shown in FIG. 4 with an RFID tag disposed in yet another location.
Figure 7:
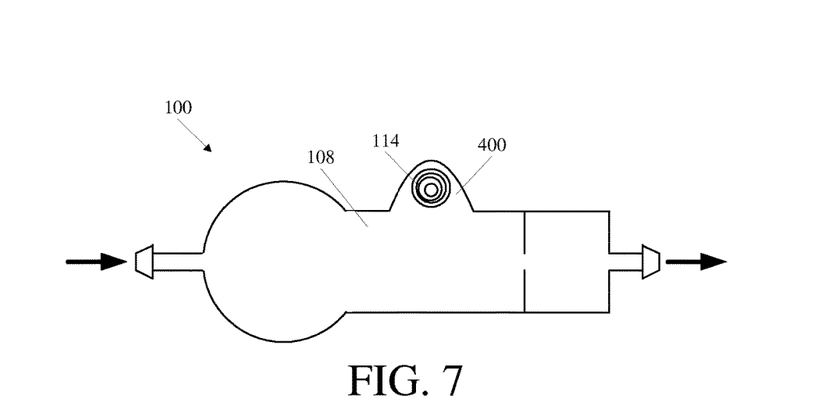
FIG. 7 is a schematic view of another embodiment of an implantable valve having an RFID tag disposed therein.

As mentioned above, the RFID tag 114 can be disposed in a wide variety of locations. For example, it can be disposed in the valve 100, disposed at a location proximate to the valve 100, or implanted at any other location within the patient associated with the valve 100, including at a location remote from the valve 100. FIG. 5 shows another schematic embodiment of the valve 100 in which the RFID tag 114 is disposed proximate to the distal end 104b of the valve 100. FIG. 6 shows an alternate schematic embodiment of the valve 100 in which the RFID tag 114 is disposed outside the valve 100, in this example embodiment proximate to the proximal end 104a of the valve 100, although the RFID tag 114 can be implanted any distance from the valve 100. FIG. 7 illustrates yet another schematic embodiment of the valve 100 where the RFID tag 114 is disposed in an offset tag housing area 400 of the reservoir 108. It should be understood that the reservoir 108 can have any size and shape, including a shape accommodating the RFID tag 114. In the embodiments shown in FIGS. 4-6, the reservoir 108 has a substantially rectangular shape, while in the embodiment shown in FIG. 7, the reservoir has a substantially circular shape at its proximal end and a substantially rectangular shape at its distal end. In other embodiments, the RFID tag 114 can be non-implantable and can be embedded or housed in a RFID bracelet, key fob, card, etc., to hold information, and issued or given to a patient.

The housing 102 can be formed from a variety of materials. In an exemplary embodiment, however, the housing 102 is formed from a flexible, biocompatible material. Suitable materials include, for example, polymers such as silicones, polyethylene, and polyurethanes, all of which are known in the art. The housing 102 can also optionally be formed from a radio-opaque material. A person skilled in the art will appreciate that the materials are not limited to those listed herein and that a variety of other biocompatible materials having the appropriate physical properties to enable the desired performance characteristics can be used.

The valve 100 and/or the RFID tag 114 can also optionally include a coating 116 that is adapted to hermetically seal all or at least a portion of the valve 100, the RFID tag 114, and/or other components such as a sensor, an antenna, a connector, etc. The coating 116 can be applied to only a portion of the RFID tag 114 that could be exposed to fluid, or it can be applied to the RFID tag 114, and optionally the valve 100. The RFID tag 114 and the valve 100 can be coated separately with different coatings or together in a single coating. In the embodiment shown in FIG. 4 in which the RFID tag 114 is disposed in the valve 100, the RFID tag 114 is preferably pre-coated prior to coupling the sensor assembly to the housing 102. Once coated, the RFID tag 114 can be appropriately positioned. An adhesive or other mating technique can be used to affix the RFID tag 114 within the housing 102, such as in the embodiment shown in FIG. 5, however, in some embodiments it can be useful to allow the RFID tag 114 to be removed from the valve 100 if necessary.

Alternatively, the valve 100 can be coated after the RFID tag 114 is disposed in the valve 100 or located elsewhere to form a protective sheath over the RFID tag 114 and the housing 102. The ports 106, 110 can be protected from any coating applied thereto, formed after the coating is applied, or be cleared of any coating applied thereto to allow fluid to flow therethrough. In other embodiments, only certain components of the valve 100 can be coated. A person skilled in the art will appreciate that a variety of other techniques can be used to seal the RFID tag 114 and/or other components of the valve 100.

The material used to form the coating 116 can vary, and a variety of techniques can be used to apply the coating. By way of non-limiting example, suitable materials include polyurethane, silicone, solvent-based polymer solutions, and any other polymer that will adhere to the components to which it is applied to, and suitable techniques for applying the coating include spray-coating or dip-coating.

Referring to FIGS. 4-8, the shape, technical specifications, and size of the RFID tag can vary widely (as can the RFID tag 114 of FIGS. 1 and 2). In many embodiments, a relatively small RFID tag can be used so as to minimize the footprint of the tag in the device, for example with dimensions in a range of about 5 mm to 10 mm, but in other embodiments, tags with dimensions of about 3 mm to 50 mm can be used and any size is possible. The RFID tag 114 can be adapted to be in communication with an external device (e.g., by having an antenna) and to store data.

The RFID tag 114 can have any shape, such as elliptical, circular, or rectangular (including square), and can have virtually any size. The RFID tag 114 can be an off-the-shelf component. The following table (Table 1) lists, by way of example only, available RFID tags suitable for use with the devices and methods described herein. Passive as well as semi-passive and active tags can be used, although semi-passive and active tags sometimes are larger than passive tags because they can incorporate an internal battery, e.g., for power purposes.

TABLE 1

| | Frequency | | | | | |
|---|---|---|---|---|---|---|
| Tag Type | 125 KHz | 5-7 MHz | 13.56 MHz | 303/433 MHz | 860-960 MHz | 2.45 GHz |
| Passive | ISO11784/5, 14223 ISO18000-2 | ISO10536 iPico DF/iPX | (ISO15693) (ISO15693) MIFARE (ISO14443) | — | ISO18000-6 Electronic Product Code ("EPC") Class 0 | ISO18000-4 Intellitag µ-chip |

TABLE 1-continued

| Tag Type | Frequency | | | | | |
|---|---|---|---|---|---|---|
| | 125 KHz | 5-7 MHz | 13.56 MHz | 303/433 MHz | 860-960 MHz | 2.45 GHz |
| | — | — | Tag-IT (ISO15693) ISO18000-3 | — | EPC Class 1 EPC GEN II Intellitag tolls (Title 21) rail (Association of American Railroads ("AAR") S918) | |
| Semi-Passive | — | — | — | — | rail (AAR S918) Title 21 | ISO18000-4 Alien BAP |
| Active | — | — | — | Savi (American National Standards Institute ("ANSI") 371.2) ISO18000-7 RFCode | — | ISO18000-4 WhereNet (ANSI 371.1) |

The RFID tag 114 can store and/or communicate various types of data. The types of data stored can be selected by a user. As indicated above, the data can be related to a valve or any other implanted device(s), a patient associated with the valve, the RFID tag, sensed or measured values (including historical values), and/or characteristics of fluid flowing through the valve or valve assembly. Non-limiting examples of data related to the valve 100 (or other devices) can include date of device manufacture, device type (e.g., fixed or programmable), device identifier code, and device maintenance history. Non-limiting examples of data related to a patient can include patient identification (e.g., name, identifying code such as Social Security Number, age, etc.), medical history information (e.g., dates of pervious doctor examination(s), disease history, etc.), and date of valve implantation. Non-limiting examples of data related to the RFID tag 114 can include available memory space, date of tag manufacture, date of tag implantation, tag type, tag identifier code, and tag maintenance history. Non-limiting examples of data related to implanted sensors or sensed characteristics can include current pressure setting (e.g., a rate of fluid flow through the valve assembly 112), previous pressure setting(s), date(s) of programming/adjustments (if the valve 100 is programmable), calibration parameter(s), settings of previous calibration parameter(s), dates of previous calibration parameter(s), reasons for modifying previous calibration parameter(s) (e.g., adverse medical reactions such as fever or headache), and drift compensation values. Also, information related to a pressure sensor, such as date of implantation, sensor type, sensor ID, values read, zeroing of the sensor, date of zeroing, specific pressure reading and date taken, can be stored. Storing and communicating characteristic data such as calibration parameters and drift compensation values can include polynomial coefficients to calculate an actual pressure value from a measured pressure value. The RFID tag 114 can store such data and allow an external RF reader to obtain a correct measurement from the valve 100 without having to depend on external storage devices.

Figure 8:
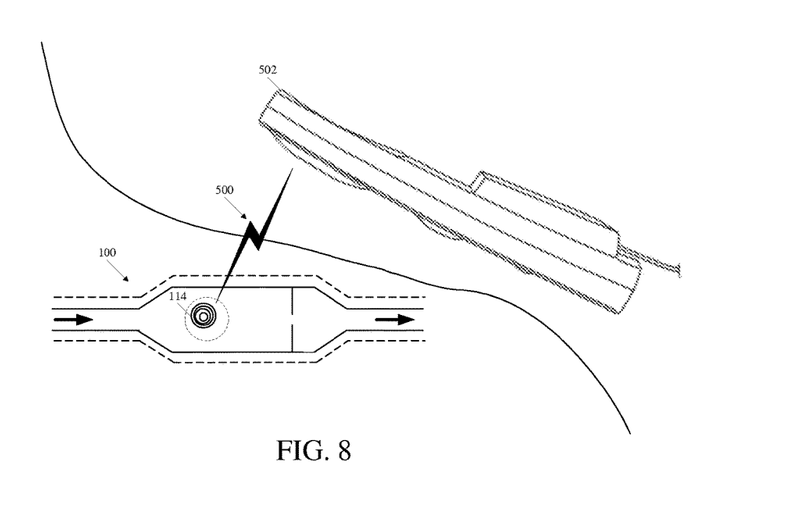
FIG. 8 is a cross-sectional view of the implantable valve of FIG. 4 implanted in a body and one exemplary embodiment of an external radio frequency telemetry reading device disposed adjacent thereto outside the body for reading a signal from the implantable valve.
Figure 9:
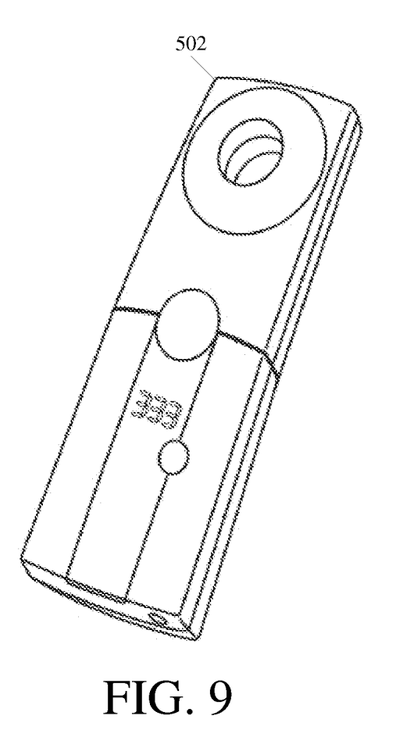
FIG. 9 is a perspective view of one exemplary embodiment of a radio frequency telemetry reading device.

As illustrated in FIG. 8, the RFID tag 114 can be adapted to interact with a wireless signal 500 from an external reading device, such as an RF telemetry device 502 (shown in more detail in FIG. 9). The reading device 502 can emit a signal 500 at one frequency or over a range of frequencies and can receive a response thereto, e.g., from the RFID tag 114 or a sensor.

Virtually any type of external reading device can be used as the RF telemetry device 502. In one exemplary embodiment, the RF telemetry device 502 can include an RF module (e.g., transmitter and receiver), a control unit (e.g., microcontroller), a coupling element to the transponder (e.g., antenna), and an additional interface (e.g., Recommended Standard (RS) 232, RS-485, Firewire, USB, Bluetooth, ZigBee, etc.) to enable communication with another external device (e.g., a personal computer). The RF telemetry device 502 can provide the power required by the RFID tag 114 to operate, e.g., through the coupling element. The RF telemetry device 502, as shown in FIG. 8, can be positioned adjacent to the RFID tag 114 to telemetrically communicate with the RFID tag 114, and thereby obtain and/or transmit data. Further information on the use of such RFID tags, including techniques for interrogating them and examples of them, can be obtained from U.S. Pat. Nos. 6,025,725, and 6,278,379, and U.S. Patent Application Publication No. 20040134991, all of which are hereby by incorporated by reference in their entireties.

In some embodiments, multiple RFID tags and/or other devices (such as the pressure sensor described above) capable of wireless communication can be implanted in a patient. Multiple RF telemetry devices can be used to communicate with these devices. Alternatively, the RF telemetry device can provide the ability to communicate with multiple devices, using different frequencies, different communication protocols, and so on. For example, the same RF telemetry device 502 can obtain data from both the pressure sensor and the RFID tag, which as mentioned previously can have antennas located in proximity to one another to facilitate such communication. In some embodiments, the RF telemetry device 502 can read identification data, such as serial numbers, from the sensor and/or the RFID tag to identify from which device it is receiving data.

In other embodiments, the RFID tag 114 can store data related to not one but a plurality of implanted medical devices, which may be devices that were implanted concurrently with the RFID tag 114 or those being "retrofitted" or "upgraded" with later implantation of an RFID tag. The RF telemetry device 502 can read from the RFID tag identification data (and other data) for each of a plurality of implanted devices. The RFID tag can store and output data so as to associate it with the implanted device to which it relates, for example via a table correlating device identifiers with data values.

In another aspect, a method for obtaining data related to medical device, such as the valve and/or pressure sensor of FIGS. 1-2, is provided. The inlet port 106 of the valve 100 can be coupled to a proximal end of a ventricular catheter 120 that has had its distal end positioned in a patient's ventricle. As shown in FIG. 8, the valve 100 can be implanted in a patient, such as a patient's shoulder area, while the typically more flexible catheter can extend through the patient to the ventricle. A drainage catheter 122 can be coupled to the outlet port 110 of the valve 100, in which the drainage catheter can extend through the patient to an area where excess fluid can safely drain. The rate of fluid flowing through the valve 100 from the inlet port 106 to the outlet port 110 can be controlled by the valve assembly 112. Data related to the valve 100 can be obtained at an external reading device (e.g., using the RF telemetry device 502) from an antenna coupled to the RFID tag 114 that is associated with the valve 100.

In the embodiment shown in FIG. 8, the RFID tag 114 is disposed in a valve 100 implanted in a shoulder area of a patient (shown for simplicity without catheters in communication with either of the ports 106, 110). However, it should be understood that the valve can be implanted virtually anywhere, for example subcutaneously behind the ear, or on the head, torso, etc. Further, as indicated above, the RFID tag 114 can be disposed outside the valve 100, at a location proximate or remote to the valve 100. The method can include implanting the RFID tag 114 concurrently or subsequently (e.g., as a replacement or retrofit) with the valve or other medical device.

In some embodiments, multiple pressure sensor assemblies can be used, each with an associated RFID tag, and the pressure sensor assemblies can be disposed at various locations relative to one another, not necessarily in a valve. The use of multiple pressure sensor assemblies can be particularly advantageous as it can allow a differential pressure of the system to be obtained. The differential pressure of the system should be equal to the operating pressure of the system, thus indicating whether the system is performing properly. CSF can flow from a patient's ventricle through a catheter (or other medical device) to the inlet port 106 and through the valve 100. Thus, the pressure of fluid flowing through the reservoir 108 of the valve 100 can correlate to the patient's ICP despite the valve's implantation at a location other than the patient's ventricle. Moreover, as indicated above, the RFID tag 114 can be disposed outside the valve 100, at a location proximate or remote to the valve 100.

Further information on wireless shunts can be obtained from U.S. patent application Ser. No. 11/931,041, entitled "Wireless Pressure Setting Indicator" by Salim Kassem, U.S. patent application Ser. No. 11/931,127, entitled "Wireless Flow Sensor" by Salim Kassem, and U.S. patent application Ser. No. 11/931,151, entitled "Wireless Pressure Sensing Shunts" by Salim Kassem, all of which are being filed on the same date as the present application and which are hereby incorporated by reference in their entirety. Also incorporated by reference in its entirety is co-pending, commonly assigned U.S. patent application Ser. No. 10/907,665, entitled "Pressure Sensing Valve" and published as U.S. Publication No. 2006-0211946 A1.

A person skilled in the art will appreciate that the various methods and devices disclosed herein can be formed from a variety of materials. Moreover, particular components can be implantable and in such embodiments the components can be formed from various biocompatible materials known in the art. Exemplary biocompatible materials include, by way of non-limiting example, composite plastic materials, biocompatible metals and alloys such as stainless steel, titanium, titanium alloys and cobalt-chromium alloys, glass, and any other material that is biologically compatible and non-toxic to the human body.

One skilled in the art will appreciate further features and advantages of the invention based on the above-described embodiments. Accordingly, the invention is not to be limited by what has been particularly shown and described, except as indicated by the appended claims. All publications and references cited herein are expressly incorporated herein by reference in their entirety.

What is claimed is:

1. A method, comprising:
    positioning a distal end of a ventricular catheter within a ventricle;
    coupling a proximal end of the ventricular catheter to a valve inlet formed on an implantable valve, and coupling a valve outlet formed on the valve to a drainage catheter such that fluid flows from the ventricle through the valve to the drainage catheter; and
    using an external reading device to obtain first data telemetrically from a pressure sensor disposed in the valve and including a first antenna, and to obtain second data telemetrically from a radio frequency identification tag disposed in the valve as a physically separate component from the pressure sensor, the radio frequency identification tag including a second antenna, and the first data being indicative of a pressure measurement obtained by the pressure sensor, and the second data including non-pressure measurement data.

2. The method of claim 1, wherein the radio frequency identification tag stores calibration data for calibrating pressure measured by the pressure sensor.

3. The method of claim 1, wherein the radio frequency identification tag stores data related to a patient medical history.

4. The method of claim 1, wherein the radio frequency identification tag is associated with a second sensor and stores data related to the second sensor.

5. The method of claim 1, further comprising adjusting a rate of fluid flow from the valve inlet to the valve outlet.

6. The method of claim 1, wherein the radio frequency identification tag stores a pressure measurement obtained by the pressure sensor disposed within the valve.

7. The method of claim 6, further comprising communicating with the pressure sensor and the radio frequency identification tag at a same frequency using the external reading device.

8. The method of claim 1, further comprising obtaining stored data telemetrically from the radio frequency identification tag by positioning the external reading device in proximity to the radio frequency identification tag.

9. The method of claim 1, further comprising programming the radio frequency identification tag with the external reading device.

10. The method of claim 1, wherein obtaining the second data includes obtaining data related to any of calibration data for the pressure sensor, patient data, patient clinical history, identification data for the valve, and identification data for the pressure sensor disposed within the valve.

11. The method of claim 1, wherein the second data includes at least one of data identifying the valve, data identifying a type of the valve, data indicative of a sensed parameter other than pressure, data identifying a patient in which the valve is implanted, data identifying the pressure sensor, data indicative of a medical history of a patient in which the valve is implanted, and drift compensation data for the pressure sensor.

12. The method of claim 1, wherein the second data includes calibration data for the pressure sensor, and the method further comprises using the obtained calibration data to telemetrically calibrate the pressure sensor.

13. The method of claim 1, further comprising implanting a second pressure sensor at a location outside the implantable valve; and using the external reading device to obtain second data telemetrically from the radio frequency identification tag, the second data being indicative of a pressure measurement obtained by the second pressure sensor.

14. The method of claim 1, wherein the external reading device includes a single external reading device that obtains the first data and the second data.

15. The method of claim 1, wherein the external reading device includes a first external reading device that obtains the first data and a second external reading device that obtains the second data.

16. A method, comprising:

implanting a valve in a patient such that a proximal end of a ventricular catheter is coupled to a valve inlet of the valve, a distal end of the ventricular catheter is positioned within a ventricle of the patient, and a valve outlet of the implanted valve is coupled to a drainage catheter such that fluid flows from the ventricle through the valve to the drainage catheter;

wherein a pressure sensor including a first antenna is disposed in the implanted valve, the pressure sensor being configured to communicate first data telemetrically to an external reading device using the first antenna, the first data being indicative of a pressure measurement obtained by the pressure sensor; and wherein a radio frequency identification tag including a second antenna is disposed in the implanted valve, the radio frequency identification tag being a physically separate component from the pressure sensor, the radio frequency identification tag being configured to communicate second data telemetrically to the external reading device using the second antenna, the second data including non-pressure measurement data.

17. A method, comprising:

implanting a valve in a patient such that a proximal end of a ventricular catheter is coupled to a valve inlet of the valve, a distal end of the ventricular catheter is positioned within a ventricle of the patient, and a valve outlet of the implanted valve is coupled to a drainage catheter such that fluid flows from the ventricle through the valve to the drainage catheter, the valve including a first pressure sensor disposed therein; and implanting a second pressure sensor at a location external to the implanted valve;

wherein a radio frequency identification tag is disposed in the implanted valve, the radio frequency identification tag being configured to telemetrically communicate first data indicative of pressure sensed by the first pressure sensor to an external reading device, and being configured to telemetrically communicate second data indicative of pressure sensed by the second pressure sensor telemetrically to the external reading device.

* * * * *